United States Patent
Palepu et al.

(10) Patent No.: US 9,662,342 B2
(45) Date of Patent: May 30, 2017

(54) FORMULATIONS OF CYCLOPHOSPHAMIDE LIQUID CONCENTRATE

(71) Applicant: AuroMedics Pharma LLC, Dayton, NJ (US)

(72) Inventors: Nagesh R. Palepu, Southampton, PA (US); Philip Christopher Buxton, Great Dunmow (GB)

(73) Assignee: AUROMEDICS PHARMA LLC, East Windsor, NJ (US)

( * ) Notice: Subject to any disclaimer, the term of this patent is extended or adjusted under 35 U.S.C. 154(b) by 56 days.

(21) Appl. No.: 14/702,320

(22) Filed: May 1, 2015

(65) Prior Publication Data

US 2015/0320775 A1 Nov. 12, 2015

Related U.S. Application Data

(60) Provisional application No. 61/991,247, filed on May 9, 2014.

(51) Int. Cl.
| | | |
|---|---|---|
| *A61K 31/664* | (2006.01) | |
| *A61K 47/12* | (2006.01) | |
| *A61K 47/10* | (2017.01) | |
| *A61K 9/00* | (2006.01) | |
| *A61K 9/08* | (2006.01) | |
| *A61K 31/675* | (2006.01) | |

(52) U.S. Cl.
CPC .......... *A61K 31/664* (2013.01); *A61K 9/0019* (2013.01); *A61K 9/08* (2013.01); *A61K 31/675* (2013.01); *A61K 47/10* (2013.01); *A61K 47/12* (2013.01)

(58) Field of Classification Search
None
See application file for complete search history.

(56) References Cited

U.S. PATENT DOCUMENTS

| | | | |
|---|---|---|---|
| 3,018,302 A | 1/1962 | Arnold et al. | |
| 4,879,286 A | 11/1989 | Alam et al. | |
| 5,137,730 A * | 8/1992 | Dennis ................. | A61K 9/2013 424/464 |
| 2006/0159713 A1 | 7/2006 | Brittain et al. | |
| 2006/0188530 A1* | 8/2006 | Yoo ...................... | A61K 9/0095 424/400 |
| 2010/0041767 A1 | 2/2010 | Alonso et al. | |
| 2010/0323020 A1* | 12/2010 | Gokhale et al. .............. | 424/489 |
| 2014/0005148 A1* | 1/2014 | Neelakantan et al. .......... | 514/90 |

OTHER PUBLICATIONS

Friedman, Journal of the American Chemical Society, vol. 87, No. 21, pp. 4978-4979, 1965.
D. Brooke, et al., Effect of Briefly Heating . . . , American Journal of Hospital Pharmacy, vol. 32, pp. 44-45, 1975.
Veronique Gilard, et al., Chemical and Biological Evaluation of Hydrolysis . . . , J. Med. Chem, vol. 37, pp. 3986-3993, 1994.
K. Pankiewicz, et al., Synthesis and Absolute Configuration Assignments . . . , Journal of the American Chemical Society, vol. 101, No. 26, pp. 7712-7718.
Jiban K. Chakrabarti, et al., Studies on the Hydrolysis of Cyclophosphamide . . . , Department of Chemistry Brandeis University and Chemical Research Laboratory . . . , Journal of Heterocyclic Chem., vol. 10, No. 1, pp. 55-58, 1973.

* cited by examiner

*Primary Examiner* — San-Ming Hui
*Assistant Examiner* — Andrew Lee
(74) *Attorney, Agent, or Firm* — Lucas & Mercanti, LLP

(57) ABSTRACT

Cyclophosphamide containing compositions preferably in the form of solutions having extended stability are disclosed. The compositions contain cyclophosphamide, ethanol and an ethanol soluble acidifying agent such as citric acid. Ready to dilute or ready to use cyclophosphamide containing composition of the invention maintain high levels cyclophosphamide content after about 18 or 24 months at a temperature of about 5° C.

19 Claims, No Drawings

FORMULATIONS OF CYCLOPHOSPHAMIDE LIQUID CONCENTRATE

CROSS REFERENCE TO RELATED APPLICATIONS

This application claims the benefit of priority from U.S. Provisional Application No. 61/991,247 filed May 9, 2014, the contents of which are incorporated herein by reference.

FIELD OF THE INVENTION

The present invention is directed to improved cyclophosphamide formulations and methods of making the same.

BACKGROUND OF THE INVENTION

Cyclophosphamide is the generic name for 2-[bis(2-chloroethyl)amino]-tetrahydro-2H-1,3,2-oxazaphosphorine-2-oxide monohydrate, a widely used antineoplastic drug chemically related to the nitrogen mustards. Cyclophosphamide is one example of a group of cyclic phosphoric acid ester amides which were disclosed and claimed in U.S. Pat. No. 3,018,302 granted Jan. 23, 1962 to H. Arnold et al. Cyclophosphamide is sold under the proprietary name CYTOXAN. ENDOXAN and NEOSAR are other proprietary names for similar pharmaceutical formulations of cyclophosphamide. The commercial cyclophosphamide product is a sterile dry mixture of cyclophosphamide monohydrate.

While the crystal form of cyclophosphamide used in these products is the monohydrate, which is the easiest to isolate and with which to work, the anhydrous form also exists. As used herein, the term "cyclophosphamide" refers generically to the drug substance regardless of the crystal form, the term "cyclophosphamide monohydrate" refers specifically to the monohydrate and the term "anhydrous cyclophosphamide" refers to the anhydrous form. The monohydrate form is preferred for pharmaceutical processing, since the anhydrous form readily picks up water to form the monohydrate when exposed to a relative humidity of about 20-30% or higher at about 25° C. While the monohydrate is stable, nonetheless, under dry conditions (e.g. a relative humidity of about 20% or less) the monohydrate begins to lose this water of hydration which can reduce stability during manufacturing. Because of stability limitations which may be due in part to ready inter-conversion between the anhydrous and monohydrate forms, it is recommended that storage temperatures for cyclophosphamide products not exceed 30° C. (86° F.), and preferably be stored at or below about 25° C. (77° F.).

Currently, the parenteral dosage formulations of cyclophosphamide consist of sterile packaged dry powder fill of cyclophosphamide monohydrate. The sterile powder is dissolved in water or normal saline prior to administration, which can be oral as well as parenteral. It is intended that the solution itself be administered promptly after being prepared but it is satisfactory for use up to several hours after preparation. During processing and/or storage of the currently available dry powder formulation, the product can acquire a glassy and/or sticky nature resulting in an undesirable material with prolonged dissolution times and decreased potency. This deterioration is more pronounced as storage time is extended or if the upper limit of the storage temperature range is exceeded.

A common practice used with constitution of sterile solids by a suitable aqueous vehicle consists of warming the solution in the container to expedite the dissolution process, especially when the solids dissolve slowly. A study examining the effect of briefly heating cyclophosphamide solutions was reported by D. Brooke, et al. in American Journal of Hospital Pharmacy, 32:44-45 (1975). This study concluded that warming vials of cyclophosphamide in order to facilitate dissolution after adding an aqueous vehicle could decrease the potency of the final injectable product. In summary, these stability limitations and dissolution difficulties can often result in clinical usage of sub-potent cyclophosphamide solutions.

SUMMARY OF THE INVENTION

Therefore, an object of the present invention is to provide liquid cyclophosphamide containing compositions which have improved solubility characteristics and enhanced appearance, while maintaining a potency appropriate for a pharmaceutical dosage form.

The invention includes cyclophosphamide-containing compositions such as pharmaceutically acceptable cyclophosphamide containing solutions having extended stability. The compositions include: a) cyclophosphamide; b) ethanol; and c) an ethanol soluble acidifying agent.

Some preferred aspects of the invention include solvent systems which contain ethanol and further excipients such as citric acid, calcium chloride dihydrate or a combination thereof.

DETAILED DESCRIPTION OF THE INVENTION

As mentioned above, the invention includes pharmaceutically acceptable cyclophosphamide containing compositions, preferably in liquid form having extended stability. Some broad aspects of the invention include cyclophosphamide containing compositions which comprise cyclophosphamide, ethanol and an ethanol soluble acidifying agent. Preferably, the cyclophosphamide containing compositions are in the form of a substantially non-aqueous, ethanolic solution which is ready for dilution and administration to a patient in need thereof.

The cyclophosphamide included in the compositions of the present invention is one of the pharmaceutically acceptable forms of the molecule such as cyclophosphamide monohydrate, USP or cyclophosphamide anhydrate.

The ethanol included in the compositions of the present invention can be any ethanol, preferably an ethanol which meets the requirements of the U.S. or European Pharmacopoeia. In certain aspects of the invention the ethanol is anhydrous.

The ethanol soluble acidifying agents included in the compositions described herein can, in some embodiments, have pKa value less than 5.0. In many aspects, the ethanol soluble acidifying agents are organic or inorganic acids which are suitable for inclusion in parenteral compositions. For example, suitable acids include without limitation organic acids such as succinic, acetic, lactic and tartaric acids and inorganic acids such as phosphoric, sulphuric, hydrochloric and nitric acids. In some preferred aspects, the acidifying agent included in the compositions is in anhydrous form. One particularly preferable acidifying agent is citric acid anhydrous. In alternative aspects, the acidifying agents can include a buffering agent such as pharmaceutically acceptable buffers which include, without limitation, buffers such as citrate, phosphate, acetate, sulfate and HCl based buffers. Generally, the amount of ethanol soluble acidifying agent included in the compositions is an amount which is sufficient to keep the pH of the solution when diluted in IV fluids at 20 mg/ml cyclophosphamide concentration is between about 3 to about 4.

The amount of ethanol soluble acidifying agent which is sufficient in some aspects of the invention will range from about 0.2 to about 2% W/V of the composition prior to dilution to the volume as administered to a patient. In some aspects, the amount of acidifying agent is between 1.0 and 1.8% W/V with about 1.6 being preferred. Alternative aspects include amounts of from about 0.4 to about 0.8% % W/V and amounts from about 0.4 to about 0.6% % W/V. Illustratively, this can be equivalent to concentrations of from about 1 to about 8 mg/ml, from about 2 to about 6 or from about 2 to about 4 mg/ml of the ethanol soluble acidifying agent in the composition (prior to dilution for patient administration). For purposes of illustration, a composition containing 200 mg/ml cyclophosphamide can contain about 4 mg/ml citric acid while a composition containing 400 mg/ml cyclophosphamide can contain about 8 mg/ml citric acid. Thus, a suitable ratio of drug to acidifying agent in the ethanol composition can be 50 mg of drug: 1 mg acidifying agent. It will be understood by those of ordinary skill that the amount of the ethanol soluble acidifying agent which is sufficient can vary somewhat depending upon the acidifying agent(s) selected. While the amount required will typically be within the above-mentioned ranges, specific amounts for any acidifying agent will be readily determined by those of ordinary skill.

The concentration of the cyclophosphamide in the inventive solutions prior to dilution and administration to patients is in many aspects from about 100 to about 600 mg/ml, or from about 250 to about 550 mg/ml. In other preferable embodiments, the cyclophosphamide concentration is about 200, 400 or 500 mg/ml. Such aspects of the invention are for storage purposes typically. As will be understood by those of ordinary skill, the highly concentrated alcohol-based compositions will typically undergo significant dilution prior to IV or parenteral administration to a patient in need thereof.

In further embodiments, the inventive cyclophosphamide containing solutions include a source of chloride ions either in addition to or in place of the ethanol soluble stabilizing agent. The amount of included is an amount which is sufficient to achieve the desired long term storage stabilizing effect on the cyclophosphamide. In many embodiments, the amount of stabilizing agent is from about 1 to about 5 mg/ml of the ready to dilute composition. Suitable sources of chloride ions are those which include chloride containing salts, such as calcium chloride dihydrate. Alternatives include without limitation, choline chloride and magnesium chloride hexahydrate. Alternatives will be apparent to those of ordinary skill.

The pharmaceutically acceptable cyclophosphamide containing solutions can also include an anti-oxidizing agent such as, for example, thioglycerol, propyl gallate, methionine, cysteine and combinations thereof. Thioglycerol is a preferred antioxidant. Useful concentrations of the antioxidant in the inventive compositions can be range from about 1 to about 8 mg/ml.

The cyclophosphamide containing compositions, i.e. solutions described herein have significantly improved shelf lives. In certain aspects of the invention, the cyclophosphamide-containing solutions maintain at least about 90% or about 95%, and alternatively, at least about 97% cyclophosphamide content after about 18 months at a temperature of about 5° C. Along with these advantages, the compositions claimed herein are distinguishable from currently marketed products because the inventive liquid formulations do not require 30 minute constitution time and can be diluted directly in the vial containing the cyclophosphamide to a concentration of 20 mg/ml or into an infusion bag.

The compositions of the present invention in some alternative aspects of the invention can include supplemental solubilizing agents such as propylene glycol in amounts from about 5 to about 30% v/v. In these alternative aspects, the amount of ethanol in the ready to dilute composition would be at least about 70% v/v or about 80% v/v. One suitable solvent system in accordance with this aspect of the invention provides cyclophosphamide compositions which contain about 70% ethanol, about 30% propylene glycol, and about 0.5% thioglycerol.

The invention further includes pharmaceutically acceptable containers containing the pharmaceutically acceptable cyclophosphamide containing solutions described herein. The containers can be single use or multiple use vials containing one or more typical doses of the drug. Broadly speaking, the containers will include cyclophosphamide solutions containing from about 0.1 g to about 4 g of the drug. Some other aspects of the invention include containers in which there are about 500 mg, about 1 gram or about 2 grams of cyclophosphamide in ethanol that are ready to dilute with an IV infusion fluid in the vial containing the drug. For example, a container or vial containing 500 mg of cyclophosphamide can include about 2.5 ml of the composition at a concentration for the cyclophosphamide of 200 mg/ml and include room therein for the diluent. Similarly, containers designed to hold 1 or 2 grams of cyclophosphamide will contain about 5 ml or 10 ml of a 200 mg/ml cyclophosphamide composition described herein and proportionally less volume when the concentrations are 400 or 500 mg/ml, i.e., a container holding 2 grams of cyclophosphamide can also be prepared using 5 ml of a 400 mg/ml cyclophosphamide composition described herein. Alternatively, containers with 1, 2 or 4 ml of a 500 mg/ml composition, optionally with space therein for dilution are also contemplated.

In use, the containers either allow for a diluent to be added thereto or be designed to allow the needed dose to be drawn up and placed into a suitable larger volume bag or other container. In either case, the containers will allow dilution of the highly concentrated solutions described herein. Suitable diluents include those well-known to those of ordinary skill such as normal saline (0.9% NaCl in water), water for injection (WFI), half-normal saline (0.45% NaCl in water), $D_5W$ and $D_5W$/normal saline, etc.

The cyclophosphamide concentrate can be filled into 25 or 30 cc vials for 500 mg strength, 50 cc vial for 1 g strength and 100 cc vial for 1 g strength. Appropriate amount of diluent or infusion fluid can be added thereto to obtain a final cyclophosphamide concentration of 20 mg/ml for direct infusion. The following table summarizes the fill volumes and the diluent required to make 20 mg/ml cyclophosphamide form various concentrates.

TABLE A

Fill volumes for various concentration of Cyclophosphamide concentrate and diluent required to make 20 mg/ml cyclophosphamide concentration

| Concentration | Fill Volume (mL) | | | Amount of diluent added (mL) | | |
|---|---|---|---|---|---|---|
| | 500 mg | 1 g | 2 g | 500 mg | 1 g | 2 g |
| 200 mg/ml | 2.5 | 5 | 10 | 22.5 | 45 | 90 |
| 375 mg/ml | 1.33 | 2.67 | 5.33 | 23.67 | 47.33 | 94.67 |
| 400 mg/ml | 1.25 | 2.5 | 5 | 23.75 | 47.5 | 95 |
| 500 mg/ml | 1 | 2 | 4 | 24 | 48 | 96 |

This solution can be further diluted in IV bags to obtain 2 mg/ml solution for slow IV infusion.

The concentration of the cyclophosphamide in liquid when administered to a patient will vary according to the needs of the patient. Some suitable concentrations for administration to patients include 20 mg/ml or 2 mg ml. The ratio of drug to liquid diluent can be from about 1:1 to about 1:100.

The invention also includes methods of treating a cyclophosphamide responsive conditions in mammals. The methods include administering an effective amount of a pharmaceutically acceptable composition containing the pharmaceutically acceptable cyclophosphamide containing solutions described herein to a mammal in need thereof. The amounts of drug and frequency of administration will be apparent to those of ordinary skill. Applicants incorporate herein by reference the FDA-approved package insert documents for cyclophosphamide products.

For purposes of the present invention, maintenance of cyclophosphamide content in the solutions shall be understood to mean the amount of cyclophosphamide content as compared to the initial amount as determined by high performance liquid chromatography ("HPLC"), such as after a period of about 18 months at a temperature of from about 5° C. The amount of lost drug content is thus calculated as being based upon the original amount cyclophosphamide being present in the composition or formulation.

EXAMPLES

Example 1 Comparative

Alam et al in U.S. Pat. No. 4,879,286 disclosed solutions of cyclophosphamide for parenteral or oral administration. The formulations included cyclophosphamide is dissolved in a solution containing an organic solvent, such as a polyol, preferably propylene glycol, polyethylene glycol or glycerol, or combinations thereof. Their stability data indicated that the polyol-based non-aqueous formulations did not have adequate stability to obtain FDA approval.

To compare to the work of Alam et al, eleven formulations using different combinations of propylene glycol, polyethylene glycol and water for injection were prepared for a comparative example included in the current work. The cyclophosphamide concentration in these formulations varied from 5 mg/ml to 100 mg/ml. The tested formulations and their stability data are presented in Tables 1, 2 and 3 below.

TABLE 1

Cyclophosphamide formulations

| Solvent | Amount of solvent(%)/Formulation # | | | | | | | | | | |
|---|---|---|---|---|---|---|---|---|---|---|---|
| | 1 | 2 | 3 | 4 | 5 | 6 | 7 | 8 | 9 | 10 | 11 |
| Propylene Glycol | 25 | | 25 | | 25 | | 25 | | 50 | 80 | 80 |
| Polyethylene Glycol | | | | | | | | | | 20 | 20 |
| Glycerol | | 25 | 25 | | | 25 | 25 | | 50 | | |
| Water | 75 | 75 | 50 | 100 | 75 | 75 | 50 | 100 | | | |
| Cyclophosphamide (mg/ml) | 5 | 5 | 5 | 5 | 20 | 20 | 20 | 20 | 20 | 20 | 100 |

TABLE 2

Stability of Formulation 1-11 at Room Temperature

| Formulation | Initial | % of initial (Weeks) | | |
|---|---|---|---|---|
| | | 1 | 2 | 9 |
| 1 | 100 | 83.5 | 71.7 | |
| 2 | 100 | 80.8 | 70.2 | |
| 3 | 100 | 84.8 | 73.7 | |
| 4 | 100 | 81.4 | 69.6 | |
| 5 | 100 | 83.3 | 72.2 | |
| 6 | 100 | 81.5 | 70.1 | |
| 7 | 100 | 85.6 | 76.1 | |
| 8 | 100 | 81.8 | 70.5 | 0.1 |
| 9 | 100 | 97.6 | 94.1 | 74.4 |
| 10 | 100 | 98.9 | 97.1 | 86.6 |
| 11 | 100 | 96.7 | 88.0 | |

TABLE 3

Stability of Formulation 8-11 at 4° C.

| Formulation | Initial | % of initial (Weeks) | | | |
|---|---|---|---|---|---|
| | | 1 | 2 | 9 | 11 | 15 |
| 8 | 100 | 97.7 | 95.0 | | 87.0 | 70.8 |
| 9 | 100 | 99.4 | 99.3 | | 96.2 | |
| 10 | 100 | 99.2 | 98.5 | | 98.7 | |
| 11 | 100 | | 99.4 | 97.3 | | |

Formulations 1 to 8 contained varying amounts of water. The data indicated that the degradation levels increased in the presence of water. Formulations 9-11, like the prior art '286 patent formulations, are totally organic solvent based formulations, and showed significant degradation when stored at room temperature. The degradation was observed even under the refrigerated conditions. For example formulation 11 showed about 2.7% potency loss when stored at 4° C. for 9 weeks, which means more than 10% potency loss will be observed at the end of one year storage at 4° C. Such levels of degradation are not acceptable as commercial products. Furthermore, cyclophosphamide administered at a concentration of 20 mg/mL such as in formulations 9-11 is highly hypertonic and will cause hemolysis or other blood incompatibilities such as phlebitis in the patients. Thus, these formulations are not suitable as parenteral product.

The solution stability of cyclophosphamide at 500 mg/ml in ethanol/PEG 400, ethanol/propylene glycol and PEG 400/propylene glycol mixtures with and without citric acid was also studied. The solution stability was not satisfactory for many of the combinations as the solutions often turned yellow in color and the potency loss even at 5° C. storage was significant. Some solutions turned hazy after one month storage at 5° C. The long term stability data (18 months) of cyclophosphamide solution in various combinations of the mixed solvents are summarized in Table 4.

TABLE 4

18-month stability of Cyclophosphamide (500 mg/ml) in mixed solvent stored at 5° C.

| Solvent Combination | Concentration (mg/ml) | % of initial | Appearance |
|---|---|---|---|
| Ethanol:PG (50:50) | 381.2 | 77.8 | Hazy |
| PEG 400:PG (50:50) | 329.9 | 67.8 | Hazy |
| Ethanol:PEG 400 (50:50) | Not assayed | | Hazy |
| PEG 400:PG (90:10) | Not assayed | | Hazy |
| Ethanol:PG (50:50) with CA (8 mg/ml) | 396.3 | 79.9 | Hazy |
| PEG 400:PG (50:50) with CA (8 mg/ml) | 328.3 | 66.5 | Hazy |
| Ethanol:PEG 400 (50:50) with CA (8 mg/ml) | 427.7 | 82.3 | Hazy |
| PEG 400:PG (90:10) with CA (8 mg/ml) | Not assayed | | Hazy |
| Ethanol:PG (50:50) with TG (5 mg/ml) | 451.6 | 90.7 | Clear |
| PEG 400:PG (50:50) with TG (5 mg/ml) | Not assayed | | Hazy |
| Ethanol:PEG 400 (50:50) with TG (5 mg/ml) | 435.6 | 88.2 | Hazy |

CA: Citric acid
TG: Thio Glycerol

In order to provide suitable, ready to dilute parenteral formulations, degradation of the cyclophosphamide must be minimized as much as possible. Ideally, for cancer drugs, it is preferable that degradation not exceed more than 3-5% during the storage period whether it is 18 months or 24 months.

Example 2

Since cyclophosphamide is essentially a highly water soluble drug and Alam et al in U.S. Pat. No. 4,879,286, tested low drug concentrations, the expectation was that organic solvents would limit the solubility attainable with acceptable parenteral solvents.

In this example, studies were initiated to determine the solubility of cyclophosphamide monohydrate in pharmaceutically acceptable solvents such as propylene glycol, polyethylene glycol and ethanol. It was surprisingly found that the solubility of cyclophosphamide monohydrate was in excess of 500 mg/ml in each of these solvents. The advantage of making a 500 mg/ml solution is that when diluted to achieve the desired 20 mg/ml solution of cyclophosphamide, suitable for intravenous administration, the organic solvent concentration in the admixture is less than about 3% which is a safe level to administer intravenously.

Since these solvents provided more than adequate solubility, the stability of the solutions containing cyclophosphamide at a concentration of 500 mg/ml was examined. The data obtained from studies in pure solvents, however, was not satisfactory. Significant degradation was observed when PG and PEG 400 were used as sole solvents with the solutions turning visibly yellow in color upon storage at all temperature conditions. However the stability of cyclophosphamide in ethanol appeared to be significantly better compared to the other two solvents and the data obtained are summarized in Table 5. Although significantly better than the partly aqueous data presented by Alam and the '286 patent supra, the ethanol alone data indicated that a commercially viable product with acceptable levels of degradation would still be difficult to attain.

TABLE 5

Stability of Cyclophosphamide Liquid Concentrate in Ethanol at 25° C.

| Storage Period | CPP Content (mg/mL) | % of Initial |
|---|---|---|
| Initial | 454.6 | 100.0 |
| 1 W | 453.8 | 99.8 |
| 2 W | 453.6 | 99.8 |
| 3 W | 449.4 | 98.9 |
| 1 M | 449.2 | 98.8 |
| 2 M | 425.2 | 93.5 |

Example 3

In order to further improve the drug's stability in ethanol it was necessary to consider the degradation chemistry of cyclophosphamide. It is known that cyclophosphamide hydrolyzes in water to form four major degradation products described in the USP monograph as Related Compounds A, B, C, and D. The mechanisms involving a direct hydrolysis for RC-A and RC-C and an internal displacement of HCl for RC-B and RC-D were first proposed by Friedman (J. Amer. Chem. Soc. 1965, 87, 4978-9) and subsequently refined by Gilard et al (J. Med. Chem. 1994, 37, 3986-93) and are summarized below:

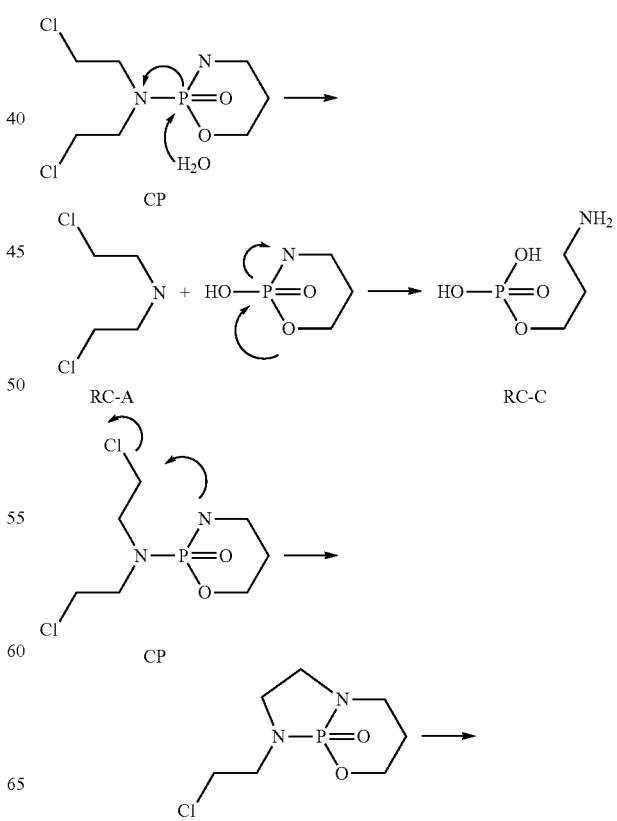

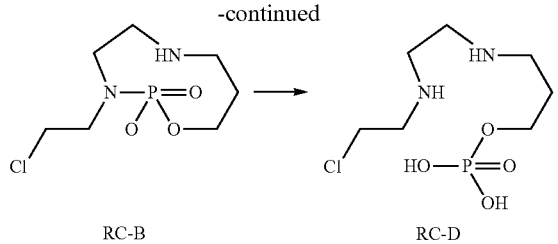

RC-B → RC-D

Gilard had reported that the aqueous stability of cyclophosphamide was best at a moderately acidic pH. Consequently, the effects of small quantities of anhydrous citric acid which is soluble in ethanol were examined. In addition, the effect of added chloride ions, which would be expected to retard the elimination of the cyclophosphamide chlorine ion, was examined. This was achieved by the addition of calcium chloride dihydrate which was soluble in ethanol. The results are described in Table 6.

TABLE 6

Stability of Cyclophosphamide (CPP) in Ethanol Containing Citric Acid and Calcium Chloride

| Excipient | Storage T° C. | Storage Period(M) | CPP Content (mg/mL) | % of Initial |
|---|---|---|---|---|
| Citric acid | | Initial | 451.9 | 100.0 |
| 2 mg/ml | 25 | 1 | 448.6 | 99.1 |
| | | 3 | 430.6 | 95.3 |
| | 15 | 6 | 437.9 | 96.9 |
| | 5 | 6 | 440.0 | 97.4 |
| | | 18 | 451.6 | 99.9 |
| Citric acid | | Initial | 425.3 | 100.0 |
| 4 mg/ml | 25 | 1 | 432.7 | 101.7 |
| | | 3 | 413.8 | 97.3 |
| | 15 | 6 | 419.0 | 98.5 |
| | 5 | 6 | 420.0 | 98.8 |
| | | 18 | 433.7 | 102.0 |
| Citric acid | | Initial | 453.2 | 100.0 |
| 6 mg/ml | 25 | 1 | 459.6 | 101.4 |
| | | 3 | 431.4 | 95.2 |
| | 15 | 6 | 445.0 | 98.2 |
| | 5 | 6 | 446.0 | 98.4 |
| | | 18 | 448.0 | 98.9 |
| Citric acid | | Initial | 492.1 | 100.0 |
| 8 mg/ml | 25 | 1 | 491.0 | 99.8 |
| | | 3 | 461.0 | 93.7 |
| | 15 | 6 | 467.9 | 95.1 |
| | 5 | 6 | 489.6 | 99.5 |
| | | 18 | NA | NA |
| Citric acid | | Initial | 494.2 | 100.0 |
| 10 mg/ml | 25 | 1 | 493.6 | 99.9 |
| | | 3 | 465.0 | 94.1 |
| | 15 | 6 | 465.3 | 94.2 |
| | 5 | 6 | 488.9 | 98.9 |
| | | 18 | 473.3 | 95.8 |
| Calcium | | Initial | 550.7 | 100 |
| Chloride | 25 | 1 | 551.1 | 100.1 |
| Dihydrate | | 3 | 523.9 | 95.0 |
| 2 mg/ml | 15 | 6 | 542.5 | 98.5 |
| | 5 | 6 | 545.0 | 99.0 |
| | | 18 | 545.8 | 99.1 |

The inclusion of citric acid improved the drug stability to the extent that a maximum of 97.3% of the drug content was retained after 3 months at 25° C. compared to 93.5% observed after only 2 months at 25° C. without citric acid.

The presence of calcium chloride was also beneficial, demonstrating the stabilizing effect of additional chloride ions. The presence of the dihydrate did not seem to induce any changes resulting from hydrolysis in the same way that the bound hydrate of cyclophosphamide seems to have no destabilizing effect.

The samples were then stored at 5° C. over 30 months and analyzed. The stability data are summarized in the Table 7 below:

TABLE 7

Long term Stability of Cyclophosphamide Ethanolic Solution Stored at 5° C.

| Concentration of Cyclophosphamide/citric acid | Assay time (months) | % of Cyclophosphamide retained |
|---|---|---|
| 500/0 | 32 | 89.0 |
| 500/2 | 31 | 89.1 |
| 500/4 | 31 | 89.4 |
| 500/6 | 31 | 88.6 |
| 500/8 | 30 | 93.3 |
| 500/10 | 30 | 92.4 |

Note: the above data generated by NMR analysis.

The longer term data at 5° C. indicated no essential change in drug content over a period of 18 months for the formulations, see for example samples containing 4-6 mg/mL citric acid, which indicates that such formulations are commercially desirable due to their long term stability.

Examples 4-8

A test of stability at a different concentrations and different size of the vial was conducted to observe any evaporative loss of ethanol. The stability data presented in Table 8.

TABLE 8

| Example No. | CPP/CA | mg/vial | Storage condition | | % CPP NMR | HPLC |
|---|---|---|---|---|---|---|
| 4 | 375/4.5 | 2 g/100 cc vial | 25° C. | 3 M | 90.6 | 88.3 |
| | | | | 6 M | 78.9 | 78.8 |
| | | | 15° C. | 6 M | 96.7 | 95.5 |
| | | | 5° C. | 3 M | 99.4 | 99.7 |
| | | | | 6 M | 99.3 | 99.1 |
| 5 | 500/6.0 | 2 g/10 cc vial | 25° C. | 3 M | 87.8 | 86.7 |
| | | | | 6 M | 74.5 | 74.7 |
| | | | 15° C. | 6 M | 95.7 | 95.4 |
| | | | 5° C. | 3 M | 99.3 | 100.5 |
| | | | | 6 M | 98.6 | 98.6 |
| 6 | 200/2.4 (1 g) | 1 g/50 cc vial | 25° C. | 3 M | 95.8 | 96.8 |
| | | | | 6 M | 88.4 | 89.6 |
| | | | 15° C. | 6 M | 97.7 | 97.2 |
| | | | 5° C. | 3 M | 99.7 | 99.4 |
| | | | | 6 M | 99.6 | 100.2 |
| | 200/2.4 (500 mg) | 500 mg/25 cc vial | 25° C. | 6 M | 88.2 | 88.2 |
| | | | 15° C. | 6 M | 98.0 | 98.8 |
| | | | 5° C. | 6 M | 99.5 | 99.4 |
| 7 | 200/6.0 | 500 mg/25 cc vial | 25° C. | 3 M | 95.6 | 96.7 |
| | | | | 6 M | 87.5 | 86.6 |
| | | | 5° C. | 3 M | 99.9 | 101.5 |
| | | | | 6 M | 99.7 | 100.5 |
| 8 | 375/6.0 | 1 g/50 cc vial | 25° C. | 3 M | 92.3 | 93.5 |
| | | | | 6 M | 79.8 | 81.5 |
| | | | 5° C. | 3 M | 99.4 | 101.1 |
| | | | | 6 M | 99.3 | 100.6 |

No weight loss, due to evaporation of ethanol, was observed in any of the stoppered vials at all storage conditions and time points.

What is claimed is:

1. A cyclophosphamide containing, substantially non-aqueous liquid composition having extended stability, comprising:
   a) about 100 to about 600 mg/ml of cyclophosphamide;
   b) an ethanolic solvent system consisting of ethanol; and
   c) an ethanol soluble acidifying agent;

wherein the cyclophosphamide and the ethanol soluble acidifying agent are solubilized in the ethanol and wherein the cyclophosphamide is the only pharmaceutically active ingredient.

2. The cyclophosphamide containing, substantially non-aqueous liquid composition of claim 1, wherein the ethanol soluble acidifying agent is an organic or inorganic acid.

3. The cyclophosphamide containing, substantially non-aqueous liquid composition of claim 2, wherein the ethanol-soluble acidifying agent is citric acid or anhydrous citric acid.

4. The cyclophosphamide containing, substantially non-aqueous liquid composition of claim 1, wherein concentration of the cyclophosphamide is from about 200 to about 550 mg/ml.

5. The cyclophosphamide containing, substantially non-aqueous liquid composition of claim 4, wherein concentration of the cyclophosphamide is about 200 or about 400 mg/ml.

6. The cyclophosphamide containing, substantially non-aqueous liquid composition of claim 1, wherein said cyclophosphamide is cyclophosphamide monohydrate.

7. The cyclophosphamide containing, substantially non-aqueous liquid composition of claim 3, wherein the citric acid is present in an amount of from about 0.2 to about 2.0% W/V.

8. The cyclophosphamide containing, substantially non-aqueous liquid composition of claim 7, wherein the citric acid is present in an amount of from about 0.4 to about 0.8% % W/V.

9. The cyclophosphamide containing, substantially non-aqueous liquid composition of claim 8, wherein the citric acid is present in an amount of from about 0.4 to about 0.6% % W/V.

10. The cyclophosphamide containing, substantially non-aqueous liquid composition of claim 1, further comprising a source of chloride ions.

11. The cyclophosphamide containing, substantially non-aqueous liquid composition of claim 1, further comprising an anti-oxidizing agent.

12. The cyclophosphamide containing, substantially non-aqueous liquid composition of claim 11, wherein the anti-oxidizing agent is selected from the group consisting of thioglycerol, propyl gallate, methionine, cysteine and combinations thereof.

13. The cyclophosphamide containing, substantially non-aqueous liquid composition of claim 12, wherein the anti-oxidizing agent is thioglycerol.

14. A cyclophosphamide containing, substantially non-aqueous liquid composition according to claim 1, wherein the solution maintains at least about 95% cyclophosphamide content after about 18 months at a temperature of about 5° C.

15. A cyclophosphamide containing, substantially non-aqueous liquid composition according to claim 5, wherein the solution maintains at least about 97% cyclophosphamide content after about 18 months at a temperature of about 5° C.

16. A cyclophosphamide containing, substantially non-aqueous liquid composition, consisting essentially of:
   a) cyclophosphamide;
   b) a solvent consisting of ethanol; and
   c) citric acid;
   wherein the cyclophosphamide and the citric acid are solubilized in the ethanol and wherein the cyclophosphamide is the only pharmaceutically active ingredient.

17. The cyclophosphamide containing, substantially non-aqueous liquid composition of claim 16, wherein the citric acid is anhydrous and the cyclophosphamide is cyclophosphamide monohydrate.

18. The cyclophosphamide containing, substantially non-aqueous liquid composition of claim 16, wherein the ratio of cyclophosphamide to citric acid is 50:1.

19. The cyclophosphamide containing, substantially non-aqueous liquid composition of claim 18, wherein the concentration of cyclophosphamide in the composition is either about 200 or about 400 mg/ml.

* * * * *